US009993423B2

(12) United States Patent
Quan et al.

(10) Patent No.: US 9,993,423 B2
(45) Date of Patent: Jun. 12, 2018

(54) MICRONEEDLE DEPOSITION METHOD (75) Inventors: Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days. days.

(21) Appl. No.: 14/352,397

(22) PCT Filed: Oct. 20, 2011

(86) PCT No.: PCT/JP2011/074159
§ 371 (c)(1),
(2), (4) Date: Apr. 17, 2014

(87) PCT Pub. No.: WO2013/057819
PCT Pub. Date: Apr. 25, 2013

(65) Prior Publication Data
US 2014/0257189 A1 Sep. 11, 2014

(51) Int. Cl.
*A61M 37/00* (2006.01)
*A61K 9/00* (2006.01)
*A61K 9/08* (2006.01)

(52) U.S. Cl.
CPC .............. *A61K 9/0021* (2013.01); *A61K 9/08* (2013.01); *A61M 37/0015* (2013.01); *A61M 2037/0046* (2013.01); *A61M 2037/0053* (2013.01)

(58) Field of Classification Search
CPC ................... A61K 9/0021; A61K 9/08; A61M 2037/0046; A61M 2037/0053;
(Continued)

(56) References Cited

U.S. PATENT DOCUMENTS 5,250,023 A 10/1993 Lee et al.
6,334,856 B1 1/2002 Allen et al.
(Continued)

FOREIGN PATENT DOCUMENTS

CN 101687090 A 3/2010
EP 2 153 863 A1 2/2010
(Continued)

OTHER PUBLICATIONS

Supplementary European Search Report for Application No. EP 11 87 4199 dated Apr. 10, 2015.
(Continued)

*Primary Examiner* — Deanna K Hall
(74) *Attorney, Agent, or Firm* — Cheng Law Group, PLLC (57) ABSTRACT

The present invention provides a microneedle array which holds a drug only in the microneedle portions, and a method of manufacturing the same.
The microneedle array 2A which holds the drug only on the tips of the microneedles can be manufactured by the microneedle deposition method, i.e. a) the microneedle array 2 is prepared using an water-soluble polymer as a base material; b) a drug solution 1 to be applied to the tips of the microneedle array 2 is prepared; and c) the tips of the microneedle array 2 are contacted with the drug solution 1 for a short time. When the drug solution 1 is a water solution, the biodegradable polymer is of water-soluble, and in addition to the drug, the biodegradable polymer is dissolved in the solution at high concentration, the applied drug is integrated with the microneedle so that only the drug does not fall away during insertion.

9 Claims, 3 Drawing Sheets (58) Field of Classification Search
CPC ...... A61M 2037/0023; A61M 37/0015; A61M 2037/0061
USPC ........................................................ 604/173
See application file for complete search history.

(56) References Cited

U.S. PATENT DOCUMENTS

| | | |
|---|---|---|
| 6,503,231 B1 | 1/2003 | Prausnitz et al. |
| 6,611,707 B1 | 8/2003 | Prausnitz et al. |
| 6,743,211 B1 | 6/2004 | Prausnitz et al. |
| 7,344,499 B1 | 3/2008 | Prausnitz et al. |
| 2002/0138049 A1 | 9/2002 | Allen et al. |
| 2002/0177839 A1 | 11/2002 | Cormier et al. |
| 2003/0208167 A1 | 11/2003 | Prausnitz et al. |
| 2005/0137531 A1 | 6/2005 | Prausnitz et al. |
| 2007/0225676 A1 | 9/2007 | Prausnitz et al. |
| 2009/0035446 A1 | 2/2009 | Kwon |
| 2009/0043279 A1 | 2/2009 | Kaspar et al. |
| 2009/0131905 A1 | 5/2009 | Allen et al. |
| 2010/0228203 A1 | 9/2010 | Quan et al. |
| 2010/0280457 A1* | 11/2010 | Tokumoto ............ A61K 9/0021 604/173 |
| 2010/0312191 A1 | 12/2010 | Allen et al. |
| 2011/0028905 A1 | 2/2011 | Takada |
| 2012/0150023 A1 | 6/2012 | Kaspar |
| 2014/0046262 A1 | 2/2014 | Kaspar |

FOREIGN PATENT DOCUMENTS

| | | |
|---|---|---|
| EP | 2 383 013 A1 | 11/2011 |
| JP | 3-151982 A | 6/1991 |
| JP | 2002-517300 A | 6/2002 |
| JP | 2003-238347 A | 8/2003 |
| JP | 2006-346127 A | 12/2006 |
| JP | 2008-29710 A | 2/2008 |
| JP | 2008-303162 A | 12/2008 |
| JP | 2009-507573 A | 2/2009 |
| JP | 2009-273872 A | 11/2009 |
| JP | 2010-29634 A | 2/2010 |
| JP | 2010-69253 A | 4/2010 |
| JP | 2010-94414 A | 4/2010 |
| WO | WO-99/64580 A1 | 12/1999 |
| WO | WO-00/74763 A2 | 12/2000 |
| WO | WO-2008/139648 A1 | 11/2008 |
| WO | WO-2009/021048 A2 | 2/2009 |
| WO | WO2009/066763 A1 | 5/2009 |
| WO | WO-2009/142741 A1 | 11/2009 |
| WO | WO-2010/074239 A1 | 7/2010 |

OTHER PUBLICATIONS

Daddona, Peter, "Marcoflux Transdermal Technology Development for the Delivery of Therapeutic Peptides & Proteins" Transdermal Technology, 2002, vol. 2, No. 5, pp. 54-57.
Written Opinion of the International Searching Authority (PCT/ISA/237) for Application No. PCT/JP2011/074159 dated Jan. 31, 2012. (English Translation mailed May 1, 2014).
Written Opinion of the International Searching Authority (PCT/ISA/237) for Application No. PCT/JP2011/074159 dated Jan. 31, 2012.
European Office Action for Application No. 11 874 199.0 dated Dec. 17, 2015.
European Office Action for the Application No. 11 874 199.0 dated Dec. 22, 2016.
Cellulose, Microcrystalline and Carboxymethylcellulose Sodium, Handbook of Pharmaceutical Excipients, 2016, XP055329884, 5 pages.
Quan, Ying-Shu et al., "The Course of Development and Manufacturing for Microneedle, Yakuzaigaku", The Academy of Pharmaceutical Science and Technology, 2009, vol. 69, No. 4, pp. 272-276 (English Translation).

* cited by examiner

(a) Before Deposition (b) Contacting Depth 150μm (c) Contacting Depth 250μm

MICRONEEDLE DEPOSITION METHOD

TECHNICAL FIELD

The present invention relates to a microneedle deposition method for giving modification effects and/or functional effects on a skin surface and/or stratum corneum.

BACKGROUND ART

As a method of administering a drug to a human body, oral administration and transdermal administration are often used. Injection is a typical transdermal administration method. However, injection is a procedure which takes time and labor of specialists such as physicians and nurses, is painful and is likely to cause an infection of AIDS, hepatitis B etc. so that many people do not welcome the procedure. In contrast, a transdermal administration method without pain using a microneedle array has been recently attracting attention (Non-patent Document 1).

In transdermal administration of a drug, stratum corneum works as a barrier to drug permeation so that only applying a drug on a skin surface cannot cause enough permeability. In contrast, perforation of corneum by using a minute needle, i.e. a microneedle can remarkably improve efficiency in drug administration compared to that in the application method. It is a microneedle array in which a large number of the microneedles are integrated on a substrate. In addition, a product in which various tapes such as an adhesive tape for adhering the microneedle array to a skin and a cover sheet for maintaining an aseptic state until its use are added to the microneedle array in order to facilitate its use is called a microneedle patch.

Herein, a tape means a film to which an adhesive agent is applied.

Initially, metals and silicon had been used as base materials for the microneedle. A method in which a skin is perforated by stainless-steel needles and a drug solution is casted so that the pores absorb the drug (Patent Document 1), and a method in which surfaces of a stainless-steel needles are coated with a drug and then the needles are inserted to administer the drug (Patent Document 2) were proposed. Furthermore, it was also proposed that a drug solution is injected by hollow microneedles made by simply micronizing injection needles (Patent Document 3).

However, there were some drawbacks as followings: the drug solution-casting method not only had low efficiency of drug incorporation but also its sterility was doubtful; in the coating method, the efficiency of drug incorporation became low due to removal of the coating drug during insertion; and in the micronized injection needle method, the structure was complicated. Furthermore, when the microneedles made of metals or silicon broke in a body, it might cause an accident and this is a drawback.

In contrast, if the microneedles are prepared with a substance which dissolves in a body, such problems can be solved (Patent Document 4). In addition, if a polymer which dissolves by moisture in a skin after transdermal administration (i.e. biosoluble polymer) is used as a material for the microneedles, the application of the microneedles to the skin allows the skin moisture to diffuse into the needles, and the needles inserted into the skin swell and then dissolve. The dissolution of the needles causes diffusion of hyaluronic acid or collagen in the skin which express an anti-wrinkle effect, or dispersion in the skin of a drug or a valuable substance previously dissolved in the needles (Patent Documents 5 and 6).

A microneedle array made of the biosoluble polymer is often manufactured by using a mold (Patent Document 5). A microneedle pattern is formed by lithography using a photosensitive resin, and then transferred for preparing a mold having concave portions for forming the microneedles. A base material of the microneedles is casted onto this mold, subsequently heated to vaporize moisture, and then the solidified material is removed from the mold to obtain the microneedle array.

Some drugs to be contained in the microneedle array are extremely expensive, or can be obtained only in minute amounts. When such an expensive and valuable drug is contained in a base material to prepare a microneedle array by a conventional method, the drug would be contained not only in the microneedle portion but also in its substrate portion (Patent Document 7). When this microneedle array is inserted into a skin, a drug contained in the microneedle portion is incorporated and diffused in a body, but the drug remaining in the substrate portion is discarded without utilization, resulting in low usage efficiency of the valuable drug.

Some trials for efficient utilization of valuable drugs are already known. In addition to the method in which the surfaces of the microneedles are coated (Patent Document 2), a method in which a drug is applied to tips of microneedles (Patent Document 8), a method in which a drug is converged to tips of needles by centrifugation while the microneedles maintain softness (Patent Document 9), and a method in which a mold is filled with a solution of a drug-containing base material, dried, and then filled with a solution of base material without drug so as to hold the drug only in tips of the microneedles (Patent Document 10), etc have been reported. The method of Patent Document 8 in which this drug is applied to the tips is characterized in that the drug is dissolved by heating it to about 100° C. and applied to the tips of the microneedles.

PRIOR ART DOCUMENTS

Patent Documents

[Patent Document 1] JP-H03151982A
[Patent Document 2] JP-2008029710A
[Patent Document 3] JP-2002517300A
[Patent Document 4] JP-2003238347A
[Patent Document 5] JP-2009273872A
[Patent Document 6] JP-2010029634A
[Patent Document 7] JP-2008-303162A
[Patent Document 8] JP-2006346127A
[Patent Document 9] JP-2009507573W
[Patent Document 10] JP-2009066763X

Non-Patent Documents

[Non-Patent Document 1] Quan Ying-Shu, Kamiyama Fumio, The Course of Development and Manufacturing for Microneedle, Yakuzaigaku; The Academy of Pharmaceutical Science and Technology. Japan; September 2009 69(4), 272-276.

SUMMARY OF THE INVENTION

Problem to be Solved

An Object of the present invention is to solve the problems in the prior art and to provide a novel method for efficiently using an expensive drug.

In the method of Patent Document 8, the drug is applied to the microneedle tips. Thus, when the drug is heated to 100° C. or higher, the expensive and valuable drug is often thermally decomposed. Consequently, heating should be avoided when the drug is applied to the microneedle tips.

Additionally, the method of Patent Document 8, since the drug is simply applied to the microneedle tips, there are problems that an adherence strength of the drug is low, and when the microneedles are inserted into a skin, an applied part is broken and the drug is removed, resulting in insufficient uptake of the drug. These problems should be solved.

Solution to Problem

The microneedle deposition method related to the present invention made to solve the above-mentioned problems is characterized in that
a) the microneedle array is prepared using an water-soluble polymer as a base material,
b) a drug solution to be applied to the tips of the microneedle array is prepared,
c) the tips of the microneedle array are contacted with the drug solution for a short time, to manufacture the microneedle array in which the drug is deposited on the tips.

For efficiently applying the drug to the tips of the microneedle array, the base material for the microneedle array and the drug solution is preferably compatible with each other. For this reason, both the drug and the base material for the microneedle are preferably water-soluble. The drug solution may be a mixture of water as a main component and an organic solvent miscible therewith. Examples for the organic solvent miscible with water are ethanol and acetone.

Furthermore, a viscosity of the drug solution is preferably increased by dissolving a water-soluble polymer in the drug solution. This is because the increase of the viscosity by dissolution of the water-soluble polymer results in the increase of the amount of the drug solution deposited on the tip of the microneedle. The concentration of the water-soluble polymer in the aqueous solution is 1-20%, preferably 2-15%. The lower the concentration of the water-soluble polymer is, the small the amount of the drug solution deposited through the contact with the needle is. In addition, if the concentration is too high, its fluidity diminishes, and the deposition cannot be smoothly conducted.

The proper concentration of the water-soluble polymer in the drug solution can be decided depending on the viscosity of the drug solution. Preferable viscosity of the drug solution for deposition of the drug ranges 1.0 dPa·s to 90 dPa·s. If the viscosity of the drug solution is less than 1.0 dPa·s, the amount of deposition is small due to very low viscosity. In addition, if it is more than 90 dPa·s, the drug solution is likely to be stringy when the needle is separated from the solution after the contact with the drug solution. Note that all the viscosities are values at room temperature (25° C.).

If the time for contacting the tips of the microneedle array with the drug solution is too long, the base material for the water-soluble microneedle is dissolved in drug solution, and thus the time is preferably 0.01 to 5 seconds.

The drug solution is prepared by combining the drug and the water-soluble polymer as a base material for the microneedle, thereby the tips are partially dissolved when the microneedle tips are soaked in the drug solution, and therefore the drug is incorporated integrally with the water-soluble polymer in the microneedle tips. Thus, in the microneedles in which the drug is integrated with the base material, the deposition part i.e. the drug is not removed during insertion into the skin, and the drug is completely incorporated into the body.

Herein, the term "integrally" means that there is no definite boundary surface between the original microneedle tip and the newly-deposited part. In the boundary part, the drug is considered to have a concentration gradient. The method characterized by such integration is called a deposition method.

The drug in the present invention is defined to include all of substances which may cause some effects by being incorporated in a body.

This method is appropriate to use when an expensive drug or a drug difficult to obtain in a large amount should be transdermally administered to a human body. For an inexpensive drug and a drug available in a large amount, the drug may be initially mixed with a base material for the microneedle to prepare a microneedle from the mixed base material according to a conventional method.

When a drug is dissolved only in organic solvents, a solution prepared by dissolving the drug in the organic solvent is mixed in an aqueous solution of a water-soluble polymer to prepare an aqueous solution of the drug, and then the same procedure can be used. Even when the drug is not completely dissolved in the water-soluble polymer and suspended in a particle form, the deposition and intracorporal administration can act in the same manner as in the case of complete dissolution of the drug if the suspension is uniform and the particle size is a few μm or less.

As an example of a drug suitable for the object of the present invention, any drug which exerts effectiveness at few mg of intracorporal administration may be the subject matter, and particularly it is effective for polymer drugs. Its example may include bioactive peptides and derivative thereof, nucleic acids, oligonucleotides, various antigen proteins, bacteria, virus fragments and the like.

Examples of the bioactive peptides include insulin, exendin-4, exendin-4 derivative, calcitonin, adrenocorticotropic hormone, parathyroid hormone (PTH), hPTH (1→34), secretin, oxytocin, angiotensin, β-endorphin, glucagon, vasopressin, somatostatin, gastrin, luteinizing hormone-releasing hormone, enkephalin, neurotensin, atrial natriuretic peptide, growth hormone, growth hormone releasing hormone, bradykinin, substance P, dynorphin, thyroid stimulating hormone, prolactin, interferon, interleukins, G-CSF, glutathione peroxidase, superoxide dismutase, desmopressin, somatomedin, endothelin, skin-related growth factors such as EGF and FGF, botulinum toxin, and salts thereof. Examples of the antigen proteins and the virus fragments include influenza antigen, tetanus antigen, diphtheria antigen, HBs surface antigen, and HBe antigen. It is necessary that these are dissolved in an aqueous drug solution of the present invention or uniformly dispersed in suspension.

Examples of the suitable base materials of the microneedle include the water-soluble natural polymer material such as hyaluronic acid, collagen and dextrin, dextran, chondroitin sulfate, gelatin, proteoglycan, etc. The synthetic polymer materials such as polyvinyl pyrrolidone, polyvinyl alcohol (partially saponified), polyacrylic acid (salt), etc. can also be used. Also, the physical properties of the microneedle can be improved by blending polymers with each other or blending with low-molecular water-soluble substances. Adding various tapes such as an adhesive tape and a cover sheet to the microneedle array manufactured as above in order to facilitate its use results in a microneedle patch containing the drug only in the tips.

In many methods as conventionally reported in which a drug is impregnated in both the needle portion and the substrate portion, even if the substrate portion is thinned, the thinness is limited and requires at least 50 μm. In that case, there is a drawback that the substrate portion contains a larger amount of drug compared to the microneedle array, and the drug in the substrate portion is not administered into the skin (Patent Document 7).

Also, there is a trial for compensating for the above-mentioned drawback, in which a base material solution containing a drug is casted onto a mold for microneedle, dried, and then the base material for the substrate is removed while the microneedles remain, to which a base material solution containing no drug is casted and dried to form a substrate (Patent Document 10). However, this method has a drawback that the drug diffuses in the base material solution of the substrate at a time of application of the base material solution and the amount of the drug in the needle parts is decreased.

For these points, see Comparative Examples 1 and 2 in Examples.

Advantageous Effects of Invention

An expensive and valuable drug is held only on microneedle tips, thereby the drug can be economically and effectively used by preventing waste of the drug due to the fact that if the drug is present in the substrate, the drug is not absorbed in a body through insertion of the microneedles into a skin.

In this method, a drug is dissolved in a solvent and deposited to the microneedle tips, and therefore the drug need not be heated. Among useful drugs, many drugs decompose by heating at around 100° C., for which the conventional methods can hardly be applied, but this method does not have such a drawback.

In a manner in which the microneedle tips are contacted with a solution containing both the drug and the base material for the microneedle to incorporate the drug into the microneedles, there is no boundary surface between the original part and the newly-applied part, and so the microneedles are integrated. When the microneedles are integrated, removal of only drug is not caused in inserting the microneedles into the skin.

In this method, for drying, air drying, air blow, hot air blow, nitrogen gas blow, etc. can be adopted as required. Also, it can be sealed with a drying agent in an aluminium pouch or the like without drying.

Additionally, in this method, the length of the needle can be adjusted by changing the time for contacting with the drug solution, the contacting depth of the needles, etc., and this is a significant characteristic of this deposition method in comparison with those of other methods.

MODE FOR CARRYING OUT THE INVENTION

Methods for contacting the microneedle tips with the drug solution include the following methods.

Figure 1:
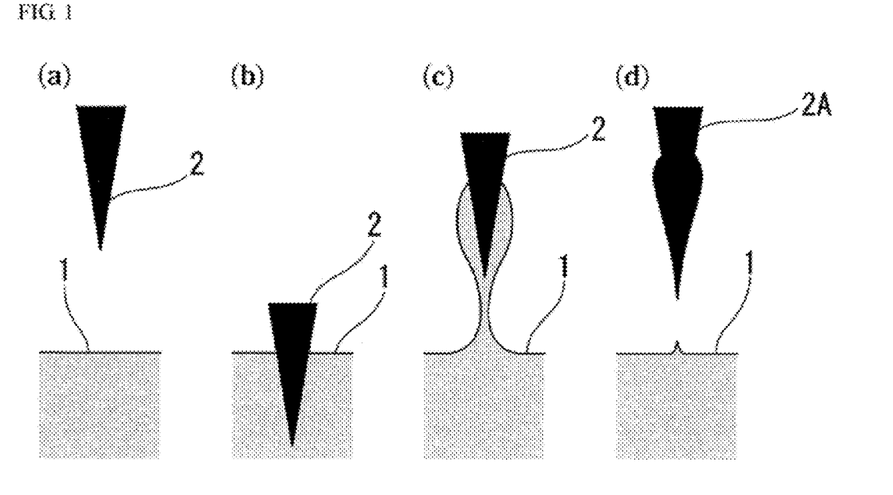
FIG. 1 shows a schematic view of the microneedle deposition method of the present invention.

(1) The microneedle array is soaked into the surface of the drug solution from above (FIG. 1).

(2) The microneedle array is placed upward, and contacted with the drug contained in a sponge from above.

(3) For contacting with the drug for a short time, the microneedle array is set sideways, on which the drug solution is poured as laminar flow from above, Although the following Examples accord to the method (1), the methods (2) and (3) can also be used.

Next, Examples of the present invention will be detailed with reference to figures, but the present invention is not limited to Examples.

Example 1

(Manufacture of Drug-Containing Microneedles by Deposition Method)

A microneedle array in Example 1 was manufactured using a mold. A mold was used, which comprises a circular truncated cone-shaped concave portions for forming microneedles, prepared by forming a circular truncated cone-shaped microneedle pattern by lithography that light-irradiates a photosensitive resin and then transferring the circular truncated cone-shaped microneedle pattern through electrocasting.

The molding concave portions for forming microneedles take in a shape of circular truncated cone having 0.16 mm of base diameter, 0.03 mm of top diameter and 0.8 mm of depth, and arranged in a reticular pattern at 0.6 mm intervals, at a rate of 250 portions per 1 $cm^2$. In addition, the microneedle array was formed in a circle with 10 mm of diameter.

As a water-soluble polymer, hyaluronic acid was used. An aqueous solution of hyaluronic acid was obtained by dissolving 13.5 pts.wt. of high-molecular-weight hyaluronic acid with weight-average molecular weight of 100,000 (Kibun Food Chemifa Co., Ltd, Trade Name: "FCH-SU", derived from culture) and 1.5 pts.wt. of low-molecular-weight hyaluronic acid with weight-average molecular weight of 10,000 (Kewpie Corporation, Trade Name: "Hyalo-Oligo", derived from culture) in 85 pts.wt. of water. This aqueous solution of hyaluronic acid was casted onto a mold and heated, then water was vaporized, and the molded articles were removed from the mold to obtain a hyaluronic acid microneedle array. The resulting microneedles reflected the shape of the mold, and took in a shape of circular truncated cone having 0.16 mm of base diameter, 0.03 mm of top diameter and 0.8 mm of height. The microneedle array had the microneedles arranged in a reticular pattern at 0.6 mm intervals, and had a 10 mm of diameter.

Bovine insulin (NACALAI TESQUE, INC.) was separately dissolved in an aqueous solution of hydrochloric acid at pH 2.5, the aqueous solution was added to the aqueous solution of hyaluronic acid to obtain a drug solution at a concentration of 1.0 unit (U)/ml. The viscosity was 25 dPa·s.

As shown in FIG. 1 (*a*), the obtained microneedle array 2 was positioned above a drug solution 1. As shown in FIG. 1 (*b*), the microneedle array 2 was lowered so that 100 μm of the microneedle tip was contacted for 1 second. Subsequently, the microneedle array 2 was pulled out as shown in FIG. 1 (c). The array was air-dried to obtain 20 pieces of microneedle arrays 2A with the tips coated with concentrated insulin as shown in FIG. 1 (d).

Microscopic observation of the obtained microneedle array 2A showed that the needle tips were swollen as shown in FIG. 1(d), and the original microneedles were thoroughly integrated with the insulin-containing hydrochloric acid as a deposition part.

An amount of insulin applied to the tips was measured by using three obtained microneedle arrays. For the measurement, Grazyme insulin-EIA TEST kit (Wako Pure Chemical Industries, Ltd.) was used. It was confirmed that 0.25 unit of insulin was contained per one microneedle array. Unevenness of the contents was within 20%.

(Blood Glucose Level Measurement Test)

Insulin was transdermally administered to rats using the manufactured microneedle array.

In diabetes model rats created by administration of streptozotocin (Body weight: about 300 g), their abdomens were dehaired. After these rats were fasted for 14 hours or longer, the microneedle array was inserted to the dehaired skin and fixed to the skin by YU-KI BAN (NITTO MEDICAL CORPORATION). Blood was sampled 0.5, 1 and 2 hours after administration of the microneedle array, and the blood glucose levels were measured. For measurement of the blood glucose levels, Glucose CII-test kit (Wako Pure Chemical Industries, Ltd.) was used. The tests were conducted in four cases.

Insulin was subcutaneously injected to rats.

After the diabetes model rats were fasted for 14 hours or longer, 0.25 units of insulin were subcutaneously injected. Blood was sampled 0.5, 1 and 2 hours after administration of insulin, and the blood glucose levels were measured. For measurement of the blood glucose levels, Glucose CII-test kit was used like Example 1. The tests were conducted four times. The tests were conducted in four cases.

As a standard of the blood glucose level measurement test, a control (no insulin) was measured.

After the diabetes model rats were fasted for 14 hours or longer, blood was sampled 0.5, 1 and 2 hours later, and the blood glucose levels were measured. For measurement of the blood glucose levels, Glucose CII-test kit was used like Example 1. The tests were conducted in four cases.

(Results and Discussion of the Blood Glucose Level Tests)

Figure 2:
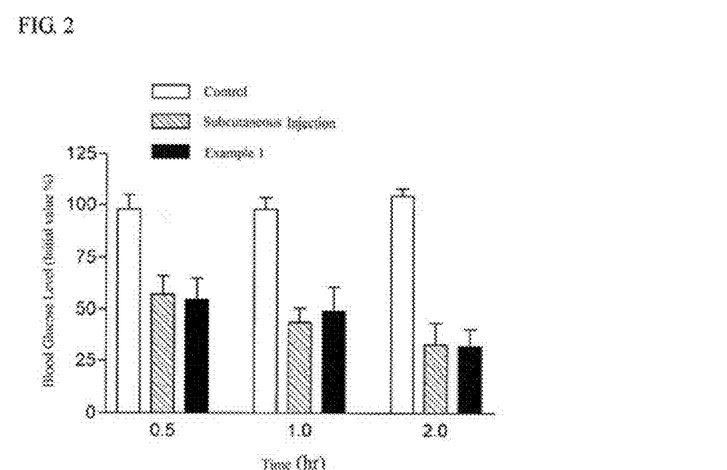
FIG. 2 shows a figure which illustrates time variation of blood glucose level after administration of insulin in a diabetes model rat.

The above-mentioned three test results were shown as time variations of blood glucose levels in FIG. 2. Each value at time zero (initial value) is set to 100 for indicating a relative value of the blood glucose level. As can be seen in this figure, the blood glucose level was lowered by the microneedle administration method like the subcutaneous injection method.

Example 2

(Manufacture of the Drug-Containing Microneedle by the Deposition Method: A Case where a Main Component is Hydrochloric Acid)

The water-soluble polymer solution was obtained by dissolving 6 pts.wt. of hydrochloric acid (Kibun Food Chemifa Co., Ltd, Weight-average molecular weight: 800,000, Trade Name: FCH-80L) and 3 pts.wt. of polyvinylpyrrolidone (BASF Japan Ltd., Trade Name: Kollidon 12 PF) in 91 pts.wt. of water. The microneedle array was manufactured by the same manipulation as in Example 1 except that the composition of the water-soluble polymer solution was different and the air drying was replaced by nitrogen gas blow for drying. The shape/size of the microneedle and the microneedle array were the same as in Example 1.

As a drug, Exendin-4 (Wako Pure Chemical Industries, Ltd.) was used. Exendin-4 is a therapeutic agent for type II diabetes and a protein with molecular weight of 4200 and has antihyperglycemic actions. In an aqueous solution containing 10 wt % of high-molecular-weight hyaluronic acid with weight-average molecular weight of 100,000 (Kibun Food Chemical Co., Ltd, Trade Name: FCH-SU, derived from culture), Exendin-4 was dissolved so that the concentration was 30 mg/ml for adjusting a drug solution.

Using a fixture, 200 μm of the microneedle array tips were contacted with the drug solution, then immediately pulled out, and dried by blowing nitrogen gas to make 20 pieces of microneedle arrays with the tips deposited with the drug.

(Manufacture of the Drug-Containing Microneedle by Deposition Method: a Case of polymethylmethacrylate)

A microneedle array comprising polymethylmethacrylate (MMA) as a base material was produced by using the same mold as in Example 1. A toluene solution of 10% MMA (Wako Pure Chemical Industries, Ltd.) was injected to the mold, and dried at 40° C. for 48 hours to produce a MMA microneedle array in the same shape as in Example 2. Using a fixture, 200 μm of the tips of the microneedle array were contacted with the same drug solution as in Example 2, then immediately pulled out, and dried by blowing nitrogen gas to produce microneedles with the tips deposited with the drug.

(Confirmation of Abundance of Exendin-4)

An abundance of the Exendin-4 was determined by enzyme immunoassay. In a solution prepared by dissolving the drug-deposited microneedle in ion-exchanged water or blood sampled from a rat vein as samples, the concentrations of the Exendin-4 in the samples were determined by Exendin-4 EIA kit (Wako Pure Chemical Industries, Ltd.).

Using three pierces of the prepared microneedle arrays, the amount of the Exendin-4 applied to the tips was measured by this method. In both cases of hyaluronic acid and MMA as main components, it was confirmed that 10 μg of Exendin-4 was contained per one microneedle array. Unevenness of the contents was within 15%.

(Blood Glucose Level Measurement Test)

Glucose tolerance test was carried out by transdermally administering the Exendin-4 to rats using the manufactured microneedle array, and the test results were compared to those of the subcutaneous injection method and the control.

Spontaneous type 2 diabetes model GK rats (8 week-old males, purchased from SHIMIZU Laboratory Supplies Co., Ltd.) were anesthetized, and then their backs were dehaired. After they were fasted for 14 hours or longer, the microneedle array was inserted to the dehaired skin and fixed to the skin by YU-KI BAN (NITTO MEDICAL CORPORATION). Thirty minutes after administration of the microneedle array, 2 g/kg body weight equivalents of glucose was intraperitoneally administered. Blood was sampled 15, 30, 60, 90 and 120 minutes after the administration, and the blood glucose levels were measured. The tests were conducted in five cases.

For measurement of the blood glucose levels, Glucose CII-test kit (Wako Pure Chemical Industries, Ltd.) was used.

(Blood Exendin-4 Level Change Test)

The blood Exendin-4 level changes were tested by transdermally administering the Exendin-4 to rats using the manufactured microneedle array, and the test results were compared to those of the subcutaneous injection method and the control.

Spontaneous type 2 diabetes model GK rats (8 week-old males, purchased from SHIMIZU Laboratory Supplies Co., Ltd.) were anesthetized, and then their backs were dehaired. After they were fasted for 14 hours or longer, the microneedle array was inserted to the dehaired skin and fixed to the skin by YU-KI BAN (NITTO MEDICAL CORPORATION). Thirty minutes after administration of the microneedle array, 2 g/kg body weight equivalents of glucose was intraperitoneally administered. Blood was sampled 15, 30, 60, 90 and 120 minutes after the administration, and the Exendin-4 levels were measured. The tests were conducted in five cases.

In both the blood glucose level measurement test and the blood drug level change test, subcutaneous injection and control test without drug administration were conducted for comparing with the transdermal administration method of the microneedle.

The subcutaneous injection method was conducted as follows. Spontaneous type 2 diabetes model GK rats (8 week-old males, SHIMIZU Laboratory Supplies Co., Ltd.) were fasted for 14 hours or longer, and then 10 μg of Exendin-4 was administered by subcutaneous injection. Thirty minutes later, 2 g/kg body weight equivalents of glucose was intraperitoneally administered. Blood was sampled 15, 30, 60, 90 and 120 minutes after the administration of glucose, and the blood glucose levels and the Exendin-4 levels were measured. The tests were conducted in five cases.

The control test was conducted as follows. Spontaneous type 2 diabetes model GK rats (the same as above) were fasted for 14 hours or longer, and 30 minutes later, 2 g/kg body weight equivalents of glucose was intraperitoneally administered. Blood was sampled 15, 30, 60, 90 and 120 minutes after the administration of glucose, and the blood glucose levels and the Exendin-4 levels were measured. The tests were conducted in three cases.

Figure 3:
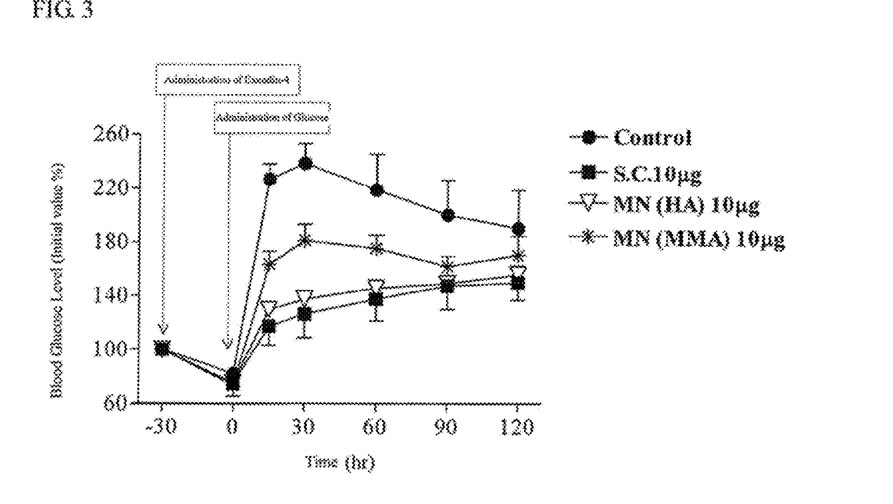
FIG. 3 shows a figure which illustrates time variation of blood glucose level after administration of Exendin-4 in a GK rat.

The time variation of blood glucose level after glucose load is shown in FIG. 3. The symbols in the figure represent the followings.
Control: Exendin-4 was not administered.
S.C. 10 μg: Exendin-4 was administered by subcutaneous injection.
MN (HA) 10 μg: Exendin-4 was administered by microneedles containing hyaluronic acid as a main component.
MN (MMA) 10 μg: Exendin-4 was administered by microneedles containing MMA.

Figure 4:
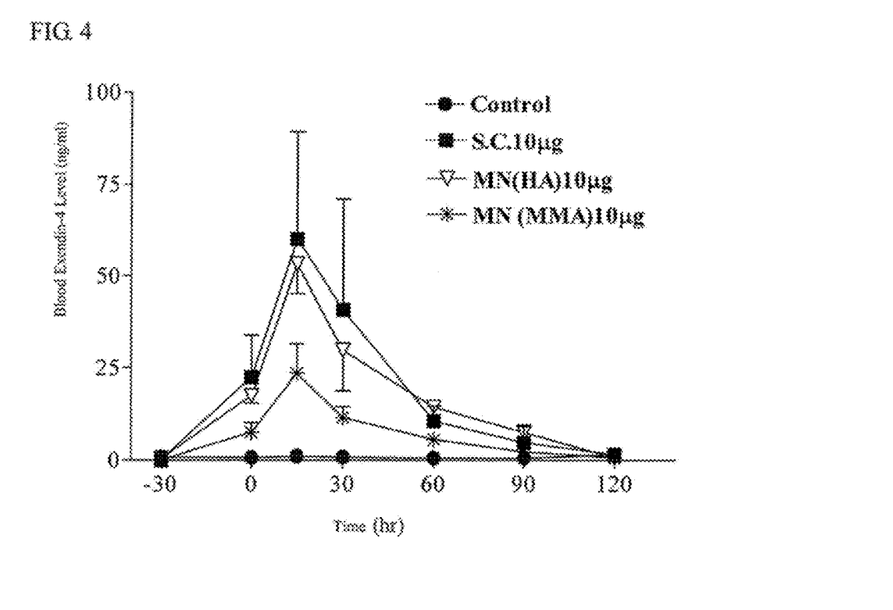
FIG. 4 shows a figure which illustrates time variation of drug concentration after administration of Exendin-4 in a GK rat.

Glucose was loaded 30 minutes after drug administration, and the subsequent time variation of the blood Exendin-4 level is shown in FIG. 4. The symbols in the figure are the same as in FIG. 3.
(Test Results and Discussion)

As shown in FIG. 3, the blood glucose level after glucose load in the Control group is rapidly increased, but increases of the blood glucose levels in the S.C. 10 μg group and the MN (HA) 10 μg group are suppressed. Meanwhile, the blood glucose level in the MN (MMA) group is lower than that in the Control group but far higher than that in the MN (HA) 10 μg group. This result shows that although the hydrochloric acid amount is 10 μg equal to the polymethylmethacrylate amount, the microneedle comprising hydrochloric acid shows higher reducing effects on the blood glucose level than of the microneedle comprising polymethylmethacrylate.

As shown in FIG. 4, in three groups to which the Exendin-4 was administered 30 minutes before glucose load, the S.C. 10 μg group and the MN (HA) 10 μg group show rapid increase of the blood Exendin-4 level and the peak concentration 45 minutes after administration (15 minutes after glucose load). Meanwhile, the blood Exendin-4 level in the MN (MMA) 10 μg group is far lower than that in the MN (HA) 10 μg group.

The results in FIGS. 3 and 4 show that the drug (Exendin-4) deposited on the hydrochloric acid microneedle shows an extremely larger amount of drug penetration in vivo through skin application of the microneedle compared to the case of application to the polymethylmethacrylate microneedle, thereby also exhibits high lowering effects on the blood glucose level. Since the administration through the MN (HA) shows the same action as of subcutaneous injection, it is demonstrated that all drugs deposited on the microneedle penetrates into the body. Meanwhile, in the case of the MN (MMA), the drug applied to the needle penetrates into the body in only one-severalth of the total amount.

This attributes to that the adherence strength of the drug applied to the MN (MMA) tip is weak, therefore the drug is removed from the microneedle when the microneedle passes through a corneum during its insertion, resulting in inhibition of systemic absorption. On the contrary, in the case of the MN (HA), the drug is integrated to the microneedle during deposition, thereby it is never removed during insertion, and thus the total amount may be absorbed into the body.

Example 3

Aqueous solutions having various concentrations of high-molecular-weight hyaluronic acid with weight-average molecular weight of 100,000 (Kibun Food Chemifa Co., Ltd, Trade Name: FCH-SU, derived from culture) were prepared, and a ratio of hyaluronic acid and water was adjusted so that the viscosities are as follows. The adjusted viscosities of the solutions were 0.5, 1.0, 5.0, 20, 50, 90, 150 dPa·s. The room temperature was 25° C. In the aqueous solutions with seven different concentrations, D&C Red No. 102 (Wako Pure Chemical Industries, Ltd.) was uniformly dissolved so that its concentration is 0.5%.

As for the microneedle array, a circle microneedle array of 1.0 cm diameter was prepared in the same way as Example 1.

To the obtained hyaluronic acid aqueous solutions with various viscosities, 150 lam of the tip of the microneedle array was contacted for 1 second, then pulled out and air-dried. In order to evaluate the amounts of the hyaluronic acid aqueous solutions deposited through the contact, one microneedle array was dissolved in 2 ml of ion-exchanged water, and the concentration of D&C Red No. 102 was measured by absorption at 510 nm. The deposition amounts of the various aqueous solutions with different concentrations of hyaluronic acid per one microneedle array were calculated from the measurement values, and the results are shown in the following table.

TABLE 1

Relationship between the viscosity and the deposition amount of the aqueous solution

| Viscosity (dPa · s) | 0.5 | 1.0 | 5.0 | 20 | 50 | 90 | 150 |
|---|---|---|---|---|---|---|---|
| Deposition amount (mg) | 0.04 | 0.16 | 0.21 | 0.24 | 0.31 | 0.44 | (*) |

(*) Since the viscosity is high and the liquid-cut property is poor, a correct value can hardly be obtained.

When the viscosity of the aqueous solution is low, the deposition amount is low. With their increase, the handling property is worse, and the shape of the needle is also irregular. It was revealed that the adequate viscosity for the aqueous solution was 1.0 to 90 dPa·s, more preferable 5.0 to 50 dPa·s.

Comparative Example 1

A microneedle array of a 1 cm diameter as shown below was produced using a mold concave portion for forming the microneedle used in Example 1.

An aqueous solution comprising 14.995 pts.wt. of hyaluronic acid (Kibun Food Chemifa Co., Ltd, Molecular weight: 800,000, Trade Name: FCH-80L) as the water-soluble polymer solution, 0.005 pts.wt. of D&C Red No. 102 as the model drug, and 85 pts.wt. of water was used. This aqueous solution of 0.3 ml was casted onto the mold, and it was dried at room temperature to mold the microneedle array (diameter: 1 cm). The microneedle array was removed from the mold, and the needle portion of the microneedle array was carefully scraped away by a sharp cutter knife under microscopic observation and separated into the needle portion and the substrate portion. Each of them was dissolved in ion-exchanged water, their absorbancies at 510 nm were measured to determine a distribution ratio of the model drug into the needle portion and the substrate portion.
Abundance in the needle portion: Abundance in the substrate portion=0.048:0.952

Consequently, it can be predicted that when the microneedle array is prepared in such a manner, a majority of the drug remains unused in the substrate portion.

Comparative Example 2

The microneedle array was formed on the mold in the same way as Comparative Example 1 except that the amount of the filled aqueous solution was 0.15 ml. Subsequently, the substrate portion in a form of coat on the surface of the mold was carefully wiped out by a wet cotton.

Subsequently, 0.3 ml of an aqueous solution without D&C Red No. 102 pigment, which comprises 15 pts.wt. of hyaluronic acid (Kibun Food Chemifa Co., Ltd, Molecular weight: 800,000, Trade Name: FCH-80L) and 85 pts.wt. of water was casted onto a mold, and dried at 40° C. to mold the microneedle array (diameter: 1 cm). The microneedle array was removed from the mold, and the needle portion of the microneedle array was carefully scraped away by a sharp cutter knife under microscopic observation and separated into the needle portion and the substrate portion. Each of them was dissolved in ion-exchanged water, their absorbancies at 510 nm were measured to determine a distribution ratio of the model drug into the needle portion and the substrate portion.
Abundance in the needle portion:Abundance in the substrate portion=0.62:0.38

The D&C Red No. 102 model drug has been originally present only on the needle portion. However, this result shows that the drug diffuses from the needle portion to the substrate portion in the step where the aqueous solution of hyaluronic acid is casted onto the mold and dried for forming the substrate portion.

Consequently, the microneedle array which holds the drug only in the microneedle portions cannot be prepared by such a method.

Example 4

An aqueous solution of high-molecular-weight hyaluronic acid with weight-average molecular weight of 100,000 (Kibun Food Chemifa Co., Ltd, Trade Name: FCH-SU, derived from culture) was prepared. The viscosity of the solution was 5.0 dPa·s. The room temperature was 25° C. In the aqueous solutions, FD4 (fluorescein-dextran, model compound, Wako Pure Chemical Industries, Ltd.) was evenly dissolved so that its concentration is 5%. As for the microneedle array, a circle microneedle array of 1.0 cm diameter was prepared using the same mold as in Example 1 except that its height is 0.65 μm.

Figure 5:
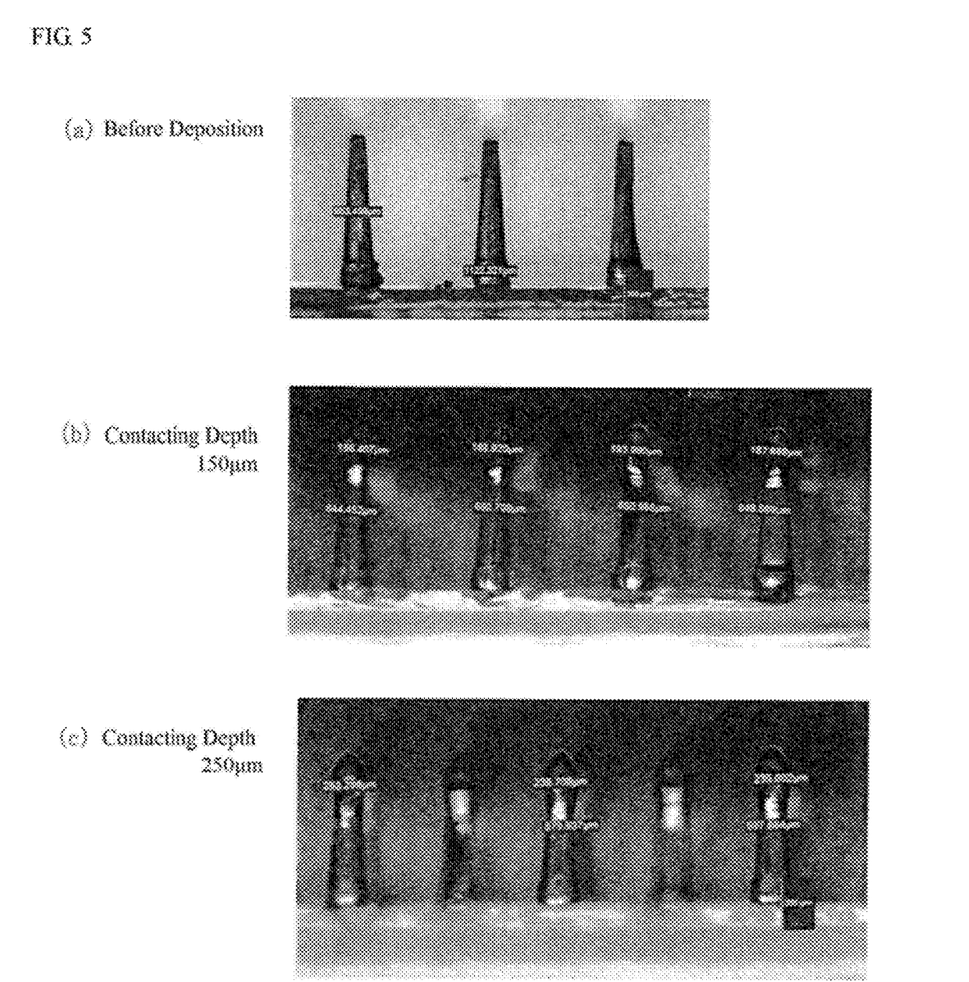
FIG. 5 shows a photograph of the deposited microneedles prepared by changing the contacting depth of the microneedle array contacted with the drug solution.

The microneedle array tips were contacted to the obtained aqueous solution of hyaluronic acid for 1 second, then pulled out, and air-dried. At this time, the needle length was adjusted by setting the contacting depth of the tip to 150 μm and 250 μm. For the microneedle with the tip deposited with the model drug, the length was shortened by partly dissolving the tip portion. The length of the needle, which was 650 μm in a non-contact state, could be changed to about 640 μm and about 570 μm by the contact of 150 μm and 250 μm of the tip respectively. See FIG. 5. The figure shows that the length of the needle could be adjusted by changing the contacting depth of the microneedle to the drug.

INDUSTRIAL APPLICABILITY

The microneedle patch according to the present invention is expected to be widely utilized in fields of medical care and cosmetology.

DESCRIPTION OF THE REFERENCE NUMERALS

1 Drug solution
2 Microneedle array
2A Microneedle array with the tips coated with concentrated insulin

The invention claimed is:

1. A microneedle deposition method of manufacturing a microneedle array in which a drug is deposited on tips thereof by the following steps:
   a) the microneedle array is prepared using a water-soluble polymer as a base material;
   b) a drug solution to be applied to the tips of the microneedle array is prepared; and
   c) the tips of the microneedle array are contacted with the drug solution for 0.01 to 5 seconds; wherein
   in addition to the drug, a water-soluble polymer is dissolved in the drug solution, characterized in that a main component of the drug solution is water,
   the water soluble polymer in the drug solution and the base material of the microneedle array are compatible with each other, and
   the tips of the microneedle array are partially dissolved when they are contacted with the drug solution, thereby incorporating the drug integrally with the water-soluble polymer in the tips of the microneedle array and creating a concentration gradient of the drug in the tips of the microneedle array such that there is no boundary surface between the original tips of the microneedle array and the drug solution.

2. The microneedle deposition method according to claim 1 characterized in that the water-soluble polymer in the drug solution and the water-soluble polymer as the base material of the microneedle array contain at least one common component.

3. The microneedle deposition method according to claim 1 characterized in that a main component of the water-soluble polymer in the drug solution and a main component of the water-soluble polymer as the base material of the microneedle array are the same.

4. The microneedle deposition method according to claim 1 characterized in that the water-soluble polymer contained in the drug solution and the water-soluble polymer as the base material of the microneedle array are the same.

5. The microneedle deposition method according to claim 1 characterized in that viscosity of the drug solution ranges 1.0 dPa·s to 90 dPa·s.

6. The microneedle deposition method according to claim 1 characterized in that the drug solution further comprises an organic solvent.

7. The microneedle deposition method according to claim 1 characterized in that a needle length of the microneedle is 100-2000 microns.

8. The microneedle deposition method according to claim 1 characterized in that the drug is any one of PTH, interferon, insulin, exendin-4, exendin derivative, EGF, FGF, botulinum toxin, various antigen proteins or virus fragments.

9. The microneedle deposition method according to claim 1 characterized in that the water-soluble polymer is any one or more selected from hyaluronic acid, dextrin, dextran, carboxymethyl cellulose, chondroitin sulfate, proteoglycan, polyacrylic acid (salt), polyvinyl pyrrolidone, and polyvinyl alcohol.

* * * * *